United States Patent
Sturm

(10) Patent No.: US 12,070,359 B2
(45) Date of Patent: Aug. 27, 2024

(54) AUTOMATED CONTROL OF INTRALUMINAL DATA ACQUISITION AND ASSOCIATED DEVICES, SYSTEMS, AND METHODS

(71) Applicant: PHILIPS IMAGE GUIDED THERAPY CORPORATION, San Diego, CA (US)

(72) Inventor: Bernhard Sturm, Davis, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 130 days.

(21) Appl. No.: 17/919,500

(22) PCT Filed: Apr. 16, 2021

(86) PCT No.: PCT/EP2021/059951
§ 371 (c)(1),
(2) Date: Oct. 17, 2022

(87) PCT Pub. No.: WO2021/213927
PCT Pub. Date: Oct. 28, 2021

(65) Prior Publication Data
US 2023/0338010 A1    Oct. 26, 2023

Related U.S. Application Data

(60) Provisional application No. 63/013,285, filed on Apr. 21, 2020.

(51) Int. Cl.
*A61B 8/00* (2006.01)
*A61B 8/04* (2006.01)
*A61B 8/06* (2006.01)

(52) U.S. Cl.
CPC .............. *A61B 8/54* (2013.01); *A61B 8/04* (2013.01); *A61B 8/06* (2013.01); *A61B 8/469* (2013.01)

(58) Field of Classification Search
CPC .... A61B 8/04; A61B 8/06; A61B 8/54; A61B 8/469
See application file for complete search history.

(56) References Cited

U.S. PATENT DOCUMENTS 7,846,101 B2   12/2010   Eberle
7,930,014 B2   4/2011    Huennekens
(Continued)

FOREIGN PATENT DOCUMENTS

EP    3417901 A       12/2018
WO    2015074018 A1   5/2015

OTHER PUBLICATIONS

International Search Report and Written Opinion of PCT/EP2021/59951, dated Jul. 6, 2021.

*Primary Examiner* — Boniface N Nganga

(57) ABSTRACT

Systems, devices, and methods for controlling intravascular data acquisition are provided. For example, a co-registration process can be used to control the start and/or stop of intravascular data acquisition. In one embodiment, a system includes a processor circuit configured to generate a roadmap of the vessel, identify a region of interest of the vessel on the roadmap, determine whether the intravascular data acquisition device has entered the region of interest, and control the intravascular data acquisition device to obtain intravascular data of the region of interest. The processor can then output, to a display device, a graphical representation of the intravascular data of the region of interest.

20 Claims, 10 Drawing Sheets

(56) References Cited

U.S. PATENT DOCUMENTS

| | | |
|---|---|---|
| 8,298,147 B2 | 10/2012 | Huennekens |
| 9,095,308 B2 | 8/2015 | Florent |
| 9,770,172 B2 | 9/2017 | Sturm |
| 2006/0241465 A1 | 10/2006 | Huennekens |
| 2010/0228076 A1* | 9/2010 | Blank .................. A61B 6/5217 600/18 |
| 2011/0319752 A1* | 12/2011 | Steinberg ............... A61B 6/541 600/424 |
| 2014/0276085 A1 | 9/2014 | Miller |

* cited by examiner

AUTOMATED CONTROL OF INTRALUMINAL DATA ACQUISITION AND ASSOCIATED DEVICES, SYSTEMS, AND METHODS

TECHNICAL FIELD

The present invention generally relates to the acquisition of intraluminal data, and in particular to automated acquisition of intraluminal data. More specifically, the present disclosure is directed to methods, systems, and devices for automated acquisition of intraluminal data using external image data.

BACKGROUND

Intraluminal data acquisition is a widely used technique in interventional cardiology as a diagnostic tool for assessing a diseased vessel, such as an artery, within the human body to determine the need for treatment, to guide the intervention, and/or to assess its effectiveness. For example, pressure and/or flow measurements can be obtained at various locations along a blood vessel to assess the vessel's performance and identify narrowed regions and potential blockages. Intravascular devices such as pressure-sensing guide wires and/or catheters may be used to pressure measurements from within blood vessels. In another example, intraluminal imaging, such as intravascular ultrasound (IVUS) imaging or optical coherency tomography (OCT) can be used to obtain imaging data of the vessel to identify lesions or blockages.

During an intravascular diagnostic procedure, an intravascular device is navigated to a region of the vasculature, such as the coronary arteries, under external imaging (e.g., angiography and/or fluoroscopy). The physician typically guides the device to a particular region of interest of the vasculature for assessment. For example, the physician may want to focus the assessment on a region of the vasculature that shows signs of narrowing or blockage. Once the pressure-sensing device is advanced past the region of interest, the physician initiates a pullback procedure in which the intravascular device is slowly drawn back through the vessel. During the pullback, the physician monitors the location of the intravascular device in the external images to determine when to initiate and/or terminate the data collection process. When the physician sees that the intravascular device has entered the region of interest, the physician manually initiates intravascular data acquisition. This may include pausing the pullback procedure to press a button or otherwise issue a command to begin obtaining intravascular data. Similarly, when the physician sees that the intravascular device has exited the region of interest, the physician manually terminates the intravascular data acquisition. This process is repeated for each region of interest identified at the start of the procedure.

Accordingly, current intravascular data acquisition workflows may involve multiple operators to control the movement of the intravascular device and start/stop data acquisition. Alternatively, current data acquisition workflows may involve a tedious process in which the physician pauses and restarts pullback procedures while visually monitoring the location of the intravascular device.

SUMMARY

The present disclosure is directed to automated acquisition of intraluminal data. For example, a co-registration process can be used to automate the start and/or stop of intraluminal data acquisition, thereby simplifying the diagnostic workflow. For example, according to one embodiment of the present disclosure, a processor circuit is configured to generate a roadmap of a vessel based on external image data, such as angiographic image data. The roadmap may have associated with it a predefined region of interest of the vessel. The processor is further configured to track a location of an intravascular data acquisition device, such as a pressure-sensing guidewire, while the device is moved through the vessel. When the processor determines that the device has entered the region of interest of the vessel, the processor circuit is configured to automatically initiate data acquisition. In some embodiments, the intraluminal data acquisition can also be terminated automatically by the processor circuit once the intraluminal device exits the region of interest. The processor circuit co-registers the intraluminal data with the external image data as the device is being tracked in the angiogram data, simultaneously. The process continues until all selected regions of interests are evaluated. This automated methodology can be applied and repeated to evaluation of multiple regions of interest identified within one vessel. In some embodiments, the regions of interest are identified by a user with a user interface device, such as a mouse, keyboard, or touch-screen display. In other embodiments, the processor circuit is configured to automatically identify one or more regions of interest of the vessel in the roadmap.

According to one embodiment of the present disclosure, a system for controlling intravascular data acquisition includes a processor circuit configured to: generate, using first extravascular image data of a vessel, a roadmap of the vessel; identify a region of interest of the vessel on the roadmap of the vessel; receive second extravascular image data representative of an intravascular data acquisition device positioned within the vessel; determine, based on the second extravascular image data, whether the intravascular data acquisition device has entered the region of interest; and in response to determining that the intravascular data acquisition device has entered the region of interest, control the intravascular data acquisition device to obtain intravascular data of the region of interest; and output, to a display device in communication with the processor circuit, a first graphical representation of the intravascular data of the region of interest.

In some embodiments, the processor circuit is configured to: identify, using the second extravascular image data, a radiopaque marker of the intravascular data acquisition device; determine, based on identifying the radiopaque marker, a location of the intravascular data acquisition device with respect to the roadmap of the vessel; and determine whether the intravascular data acquisition device has entered the region of interest based on the determined location. In some embodiments, the processor circuit is configured to output, to the display device, a screen display that includes: the roadmap; the first graphical representation of the intravascular data of the region of interest; a second graphical representation of the region of interest on the roadmap; and a third graphical representation of a location of the intravascular data acquisition device.

In some embodiments, the processor circuit is further configured to: receive, from a user interface device, a user input indicating an area on the roadmap; and identify the region of interest of the vessel based on the user input. In some embodiments, the user input indicates a length of the vessel on the roadmap. In some embodiments, the first extravascular image data comprises angiographic data, and the processor circuit is further configured to identify the region of interest based on image processing of the angiographic data. In some embodiments, the intravascular data comprises at least one of pressure data or flow data, and the processor circuit is further configured to compute a functional metric of the vessel at the region of interest based on the at least one of the pressure data or the flow data.

In some embodiments, the functional metric comprises at least one of fractional flow reserve (FFR) or instantaneous wave-free ratio (iFR). In some embodiments, the intravascular data comprises intravascular image data. In some embodiments, the processor circuit is further configured to: determine, based on the second extravascular image data, whether the intravascular data acquisition device has exited the region of interest; and in response to determining that the intravascular data acquisition device has exited the region of interest, stop receiving the intravascular data of the region of interest of the vessel from the intravascular data acquisition device. In some embodiments, the system further comprises the intravascular data acquisition device. In some embodiments, the intravascular data acquisition device comprises a flexible elongate member having a proximal portion and a distal portion, and a sensing component coupled to the distal portion. In some embodiments, the distal portion and sensing component are configured to be positioned within the vessel.

In some embodiments, the processor circuit is further configured to: identify a further region of interest of the vessel on the roadmap of the vessel; determine, based on the second extravascular image data, whether the intravascular data acquisition device has entered the further region of interest; and, in response to determining that the intravascular data acquisition device has entered the further region of interest, control the intravascular data acquisition device to obtain intravascular data of the further region of interest; and output, to a display device in communication with the processor circuit, a fourth graphical representation of the intravascular data of the further region of interest.

According to another embodiment of the present disclosure, a method includes: generating, using a first extravascular image data of a vessel, a roadmap of the vessel; identifying a region of interest of the vessel on the roadmap of the vessel; receiving second extravascular image data representative of an intravascular data acquisition device positioned within the vessel; determining, based on the second extravascular image data, whether the intravascular data acquisition device has entered the region of interest; and in response to determining that the intravascular data acquisition device has entered the region of interest, receiving intravascular data of the region of interest of the vessel from the intravascular data acquisition device In some embodiments, the method further comprises: identifying, using the second extravascular image data, a radiopaque marker of the intravascular data acquisition device; determining a location of the intravascular data acquisition device with respect to the roadmap of the vessel; and determining whether the intravascular data acquisition device has entered the region of interest based on the determined location. In some embodiments, the method further comprises: outputting, to a display device, a screen display that includes: the roadmap; a graphical representation of the region of interest on the roadmap; and a second graphical representation of a location of the intravascular data acquisition device. In some embodiments, the method further comprises: receiving, from a user interface device, a user input indicating an area on the roadmap; and identifying the region of interest of the vessel based on the user input.

In some embodiments, the first extravascular image data comprises angiographic data. In some embodiments, identifying the region of interest comprises identifying the region of interest based on image processing of the angiographic data. In some embodiments, the intravascular data comprises at least one of pressure data or flow data. In some embodiments, the method further comprises: computing a functional metric of the vessel at the region of interest based on the at least one of the pressure data or the flow data. In some embodiments, the functional metric comprises at least one of fractional flow reserve (FFR) or instantaneous wave-free ratio (iFR). In some embodiments, the method further comprises: determining, based on the second extravascular image data, whether the intravascular data acquisition device has entered the region of interest; and in response to determining that the intravascular data acquisition device has exited the region of interest, stopping receipt of the intravascular data of the region of interest of the vessel from the intravascular data acquisition device.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
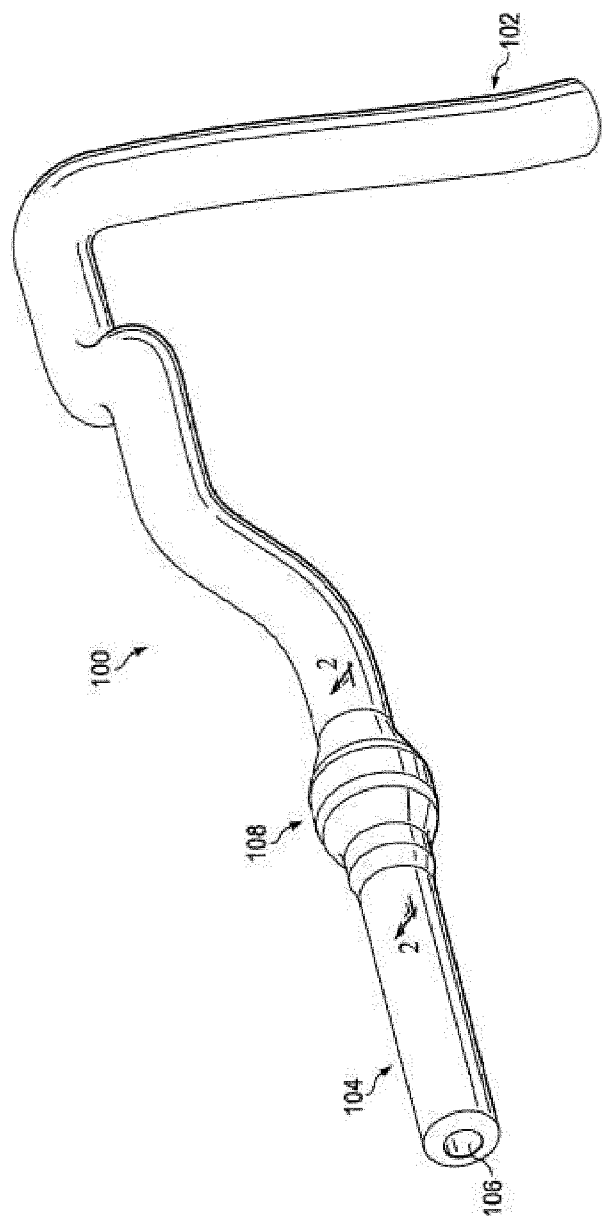
FIG. 1 shows a diagrammatic perspective view of a vessel having a stenosis according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Figure 2:
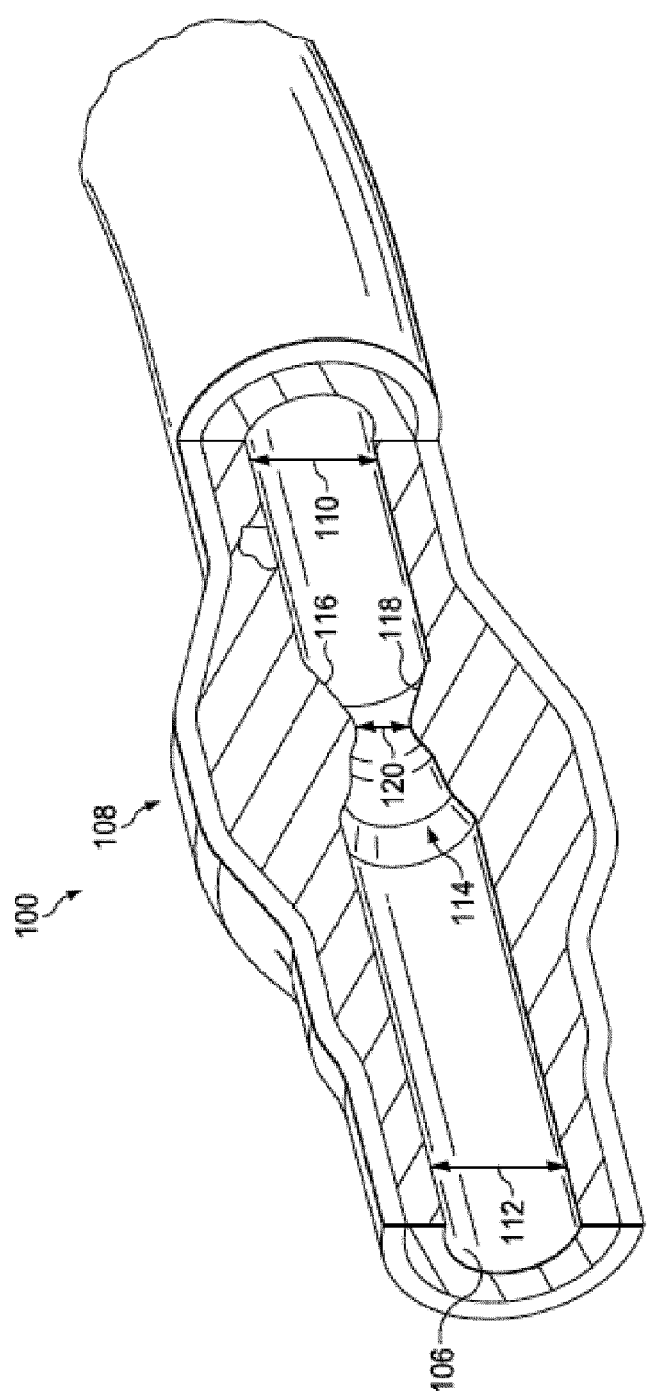
FIG. 2 shows a diagrammatic, partial cross-sectional perspective view of a portion of the vessel of FIG. 1 taken along section line 2-2 of FIG. 1.

Referring to FIGS. 1 and 2, shown therein is a vessel 100 having a stenosis according to an embodiment of the present disclosure. In that regard, FIG. 1 is a diagrammatic perspective view of the vessel 100, while FIG. 2 is a partial cross-sectional perspective view of a portion of the vessel 100 taken along section line 2-2 of FIG. 1. Referring more specifically to FIG. 1, the vessel 100 includes a proximal portion 102 and a distal portion 104. A lumen 106 extends along the length of the vessel 100 between the proximal portion 102 and the distal portion 104. In that regard, the lumen 106 is configured to allow the flow of fluid through the vessel. In some instances, the vessel 100 is a blood vessel. In such instances, the lumen 106 is configured to facilitate the flow of blood through the vessel 100. In some instances, the vessel 100 is a coronary artery. In other instances, the vessel is a peripheral vessel, such as a peripheral vein or artery.

As shown, the vessel 100 includes a stenosis 108 between the proximal portion 102 and the distal portion 104. Stenosis 108 is generally representative of any blockage or other structural arrangement that results in a restriction to the flow of fluid through the lumen 106 of the vessel 100. Embodiments of the present disclosure are suitable for use in a wide variety of vascular applications, including without limitation coronary, peripheral (including but not limited to lower limb, carotid, and neurovascular), renal, and/or venous. Where the vessel 100 is a blood vessel, the stenosis 108 may be a result of plaque buildup, including without limitation plaque components such as fibrous, fibro-lipidic (fibro fatty), necrotic core, calcified (dense calcium), blood, fresh thrombus, and mature thrombus. Generally, the composition of the stenosis will depend on the type of vessel being evaluated. In that regard, it is understood that the concepts of the present disclosure are applicable to virtually any type of blockage or other narrowing of a vessel that results in decreased fluid flow.

Referring more particularly to FIG. 2, the lumen 106 of the vessel 100 has a diameter 110 proximal of the stenosis 108 and a diameter 112 distal of the stenosis. In some instances, the diameters 110 and 112 are substantially equal to one another. In that regard, the diameters 110 and 112 are intended to represent healthy portions, or at least healthier portions, of the lumen 106 in comparison to stenosis 108. Accordingly, these healthier portions of the lumen 106 are illustrated as having a substantially constant cylindrical profile and, as a result, the height or width of the lumen has been referred to as a diameter. However, it is understood that in many instances these portions of the lumen 106 will also have plaque buildup, a non-symmetric profile, and/or other irregularities, but to a lesser extent than stenosis 108 and, therefore, will not have a cylindrical profile. In such instances, the diameters 110 and 112 are understood to be representative of a relative size or cross-sectional area of the lumen and do not imply a circular cross-sectional profile.

As shown in FIG. 2, stenosis 108 includes plaque buildup 114 that narrows the lumen 106 of the vessel 100. In some instances, the plaque buildup 114 does not have a uniform or symmetrical profile, making angiographic evaluation of such a stenosis unreliable. In the illustrated embodiment, the plaque buildup 114 includes an upper portion 116 and an opposing lower portion 118. In that regard, the lower portion 118 has an increased thickness relative to the upper portion 116 that results in a non-symmetrical and non-uniform profile relative to the portions of the lumen proximal and distal of the stenosis 108. As shown, the plaque buildup 114 decreases the available space for fluid to flow through the lumen 106. In particular, the cross-sectional area of the lumen 106 is decreased by the plaque buildup 114. At the narrowest point between the upper and lower portions 116, 118 the lumen 106 has a height 120, which is representative of a reduced size or cross-sectional area relative to the diameters 110 and 112 proximal and distal of the stenosis 108. Note that the stenosis 108, including plaque buildup 114 is exemplary in nature and should be considered limiting in any way. In that regard, it is understood that the stenosis 108 has other shapes and/or compositions that limit the flow of fluid through the lumen 106 in other instances. While the vessel 100 is illustrated in FIGS. 1 and 2 as having a single stenosis 108 and the description of the embodiments below is primarily made in the context of a single stenosis, it is nevertheless understood that the devices, systems, and methods described herein have similar application for a vessel having multiple stenosis regions.

Figure 3:
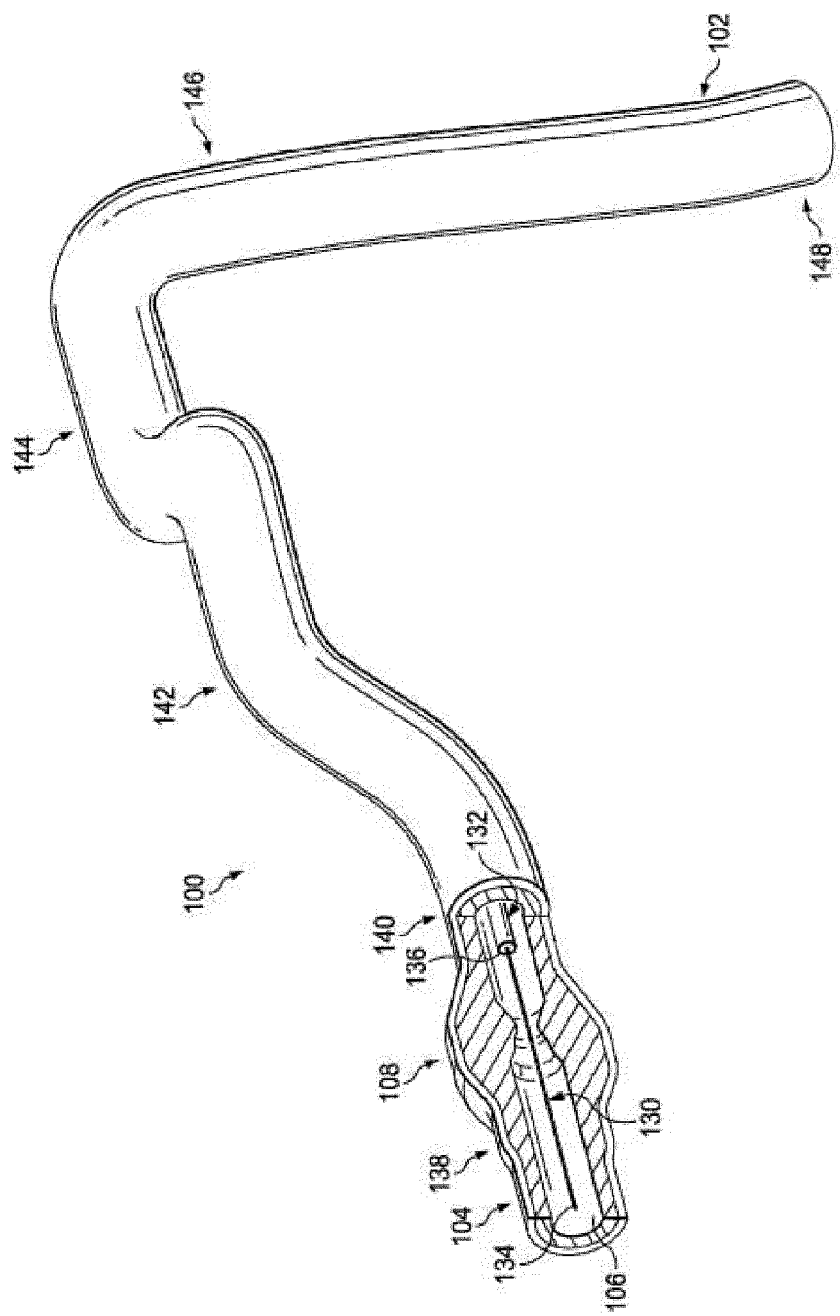
FIG. 3 shows a diagrammatic, partial cross-sectional perspective view of the vessel of FIGS. 1 and 2 with instruments positioned therein according to an embodiment of the present disclosure.

Referring now to FIG. 3, the vessel 100 is shown with instruments 130 and 132 positioned therein according to an embodiment of the present disclosure. In general, instruments 130 and 132 may be any form of device, instrument, or probe sized and shaped to be positioned within a vessel. In the illustrated embodiment, instrument 130 is generally representative of a guide wire, while instrument 132 is generally representative of a catheter. In that regard, instrument 130 extends through a central lumen of instrument 132. However, in other embodiments, the instruments 130 and 132 take other forms. In that regard, the instruments 130 and 132 are of similar form in some embodiments. For example, in some instances, both instruments 130 and 132 are guide wires. In other instances, both instruments 130 and 132 are catheters. On the other hand, the instruments 130 and 132 are of different form in some embodiments, such as the illustrated embodiment, where one of the instruments is a catheter and the other is a guide wire. Further, in some instances, the instruments 130 and 132 are disposed coaxial with one another, as shown in the illustrated embodiment of FIG. 3. In other instances, one of the instruments extends through an off-center lumen of the other instrument. In yet other instances, the instruments 130 and 132 extend side-by-side. In some particular embodiments, at least one of the instruments is as a rapid-exchange device, such as a rapid-exchange catheter. In such embodiments, the other instrument is a buddy wire or other device configured to facilitate the introduction and removal of the rapid-exchange device. Further still, in other instances, instead of two separate instruments 130 and 132 a single instrument is utilized. In some embodiments, the single instrument incorporates aspects of the functionalities (e.g., data acquisition) of both instruments 130 and 132.

Instrument 130 is configured to obtain diagnostic information about the vessel 100. In that regard, the instrument 130 includes one or more sensors, transducers, and/or other monitoring elements configured to obtain the diagnostic information about the vessel. The diagnostic information includes one or more of pressure, flow (velocity), images (including images obtained using ultrasound (e.g., IVUS), OCT, thermal, and/or other imaging techniques), temperature, and/or combinations thereof. The one or more sensors, transducers, and/or other monitoring elements are positioned at a distal portion of the instrument 130 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 134 of the instrument 130 in some instances. In some instances, at least one of the one or more sensors, transducers, and/or other monitoring elements is positioned at the distal tip of the instrument 130.

The instrument 130 includes at least one element configured to monitor pressure within the vessel 100. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Examples of commercially available guide wire products that include suitable pressure monitoring elements include, without limitation, the PrimeWire PRESTIGE® pressure guide wire, the PrimeWire® pressure guide wire, and the ComboWire® XT pressure and flow guide wire, each available from Volcano Corporation, as well as the PressureWire™ Certus guide wire and the PressureWire™ Aeris guide wire, each available from St. Jude Medical, Inc. Generally, the instrument 130 is sized such that it can be positioned through the stenosis 108 without significantly impacting fluid flow across the stenosis, which would impact the distal pressure reading. Accordingly, in some instances the instrument 130 has an outer diameter of 0.018" or less. In some embodiments, the instrument 130 has an outer diameter of 0.014" or less.

Instrument 132 is also configured to obtain diagnostic information about the vessel 100. In some instances, instrument 132 is configured to obtain the same diagnostic information as instrument 130. In other instances, instrument 132 is configured to obtain different diagnostic information than instrument 130, which may include additional diagnostic information, less diagnostic information, and/or alternative diagnostic information. The diagnostic information obtained by instrument 132 includes one or more of pressure, flow (velocity), images (including images obtained using ultrasound (e.g., IVUS), OCT, thermal, and/or other imaging techniques), temperature, and/or combinations thereof. Instrument 132 includes one or more sensors, transducers, and/or other monitoring elements configured to obtain this diagnostic information. In that regard, the one or more sensors, transducers, and/or other monitoring elements are positioned at a distal portion of the instrument 132 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 136 of the instrument 132 in some instances. In some instances, at least one of the one or more sensors, transducers, and/or other monitoring elements is positioned at the distal tip of the instrument 132.

With respect to the illustrated embodiment, similar to instrument 130, instrument 132 also includes at least one element configured to monitor pressure within the vessel 100. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Currently available catheter products suitable for use with one or more of Siemens AXIOM Sensis, Mennen Horizon XVu, and Philips Xper IM Physiomonitoring 5 and include pressure monitoring elements can be utilized for instrument 132 in some instances. Additionally, in other embodiments, the instrument 132 and/or the instrument 130 includes a flow sensor or an imaging sensor, for example.

In accordance with aspects of the present disclosure, at least one of the instruments 130 and 132 is configured to monitor a pressure within the vessel 100 distal of the stenosis 108 and at least one of the instruments 130 and 132 is configured to monitor a pressure within the vessel proximal of the stenosis. In that regard, the instruments 130, 132 are sized and shaped to allow positioning of the at least one element configured to monitor pressure within the vessel 100 to be positioned proximal and/or distal of the stenosis 108 as necessary based on the configuration of the devices. In that regard, FIG. 3 illustrates a position 138 suitable for measuring pressure distal of the stenosis 108. In that regard, the position 138 is less than 5 cm, less than 3 cm, less than 2 cm, less than 1 cm, less than 5 mm, and/or less than 2.5 mm from the distal end of the stenosis 108 (as shown in FIG. 2) in some instances. FIG. 3 also illustrates a plurality of suitable positions for measuring pressure proximal of the stenosis 108. In that regard, positions 140, 142, 144, 146, and 148 each represent a position that is suitable for monitoring the pressure proximal of the stenosis in some instances. In that regard, the positions 140, 142, 144, 146, and 148 are positioned at varying distances from the proximal end of the stenosis 108 ranging from more than 20 cm down to about 5 mm or less. Generally, the proximal pressure measurement will be spaced from the proximal end of the stenosis. Accordingly, in some instances, the proximal pressure measurement is taken at a distance equal to or greater than an inner diameter of the lumen of the vessel from the proximal end of the stenosis. In the context of coronary artery pressure measurements, the proximal pressure measurement is generally taken at a position proximal of the stenosis and distal of the aorta, within a proximal portion of the vessel. However, in some particular instances of coronary artery pressure measurements, the proximal pressure measurement is taken from a location inside the aorta. In other instances, the proximal pressure measurement is taken at the root or ostium of the coronary artery.

In some embodiments, at least one of the instruments 130 and 132 is configured to monitor pressure within the vessel 100 while being moved through the lumen 106. In some instances, instrument 130 is configured to be moved through the lumen 106 and across the stenosis 108. In that regard, the instrument 130 is positioned distal of the stenosis 108 and moved proximally (i.e., pulled back) across the stenosis to a position proximal of the stenosis in some instances. In other instances, the instrument 130 is positioned proximal of the stenosis 108 and moved distally across the stenosis to a position distal of the stenosis. Movement of the instrument 130, either proximally or distally, is controlled manually by medical personnel (e.g., hand of a surgeon) in some embodiments. In other embodiments, movement of the instrument 130, either proximally or distally, is controlled automatically by a movement control device (e.g., a pullback device, such as the Trak Back® II Device available from Volcano Corporation). In that regard, the movement control device controls the movement of the instrument 130 at a selectable and known speed (e.g., 2.0 mm/s, 1.0 mm/s, 0.5 mm/s, 0.2 mm/s, etc.) in some instances. Movement of the instrument 130 through the vessel is continuous for each pullback or push through, in some instances. In other instances, the instrument 130 is moved step-wise through the vessel (i.e., repeatedly moved a fixed amount of distance and/or a fixed amount of time). Some aspects of the visual depictions discussed below are particularly suited for embodiments where at least one of the instruments 130 and 132 is moved through the lumen 106. Further, in some particular instances, aspects of the visual depictions discussed below are particularly suited for embodiments where a single instrument is moved through the lumen 106, with or without the presence of a second instrument.

In some instances, use of a single instrument has a benefit in that it can avoid or reduce issues associated with variations in pressure measurements of one instrument relative to another. For example, in some instances, the single instrument is utilized to obtain relative changes in pressures as it is moved through the vessel such that the time period between pressure measurements is short enough to prevent any impact from any changes in pressure sensitivity of the instrument (e.g., less than 500 ms, less than 100 ms, less than 50 ms, less than 10 ms, less than 5 ms, less than 1 ms, or otherwise).

Physicians may use a variety of tools to assess and/or diagnose blood vessels. In that regard, physiological data such as pressure, flow, temperature, or other physiological measurements may be used to evaluate the function or performance of a blood vessel. Further, intravascular imaging, including IVUS and OCT, may be used to acquire greater detail on the size and structures within a blood vessel to determine a risk of blockage, for example. In assessing the vessel, the physician may desire to focus the evaluation on specific regions of the vasculature associated with a narrowing or lesion of a vessel. These regions of interest may be identified or designated for further analysis using external imaging, such as angiography. In that regard, FIGS. 4A and 4B illustrate different intravascular data acquisition devices that may be used to assess vessels.

Figure 4A:
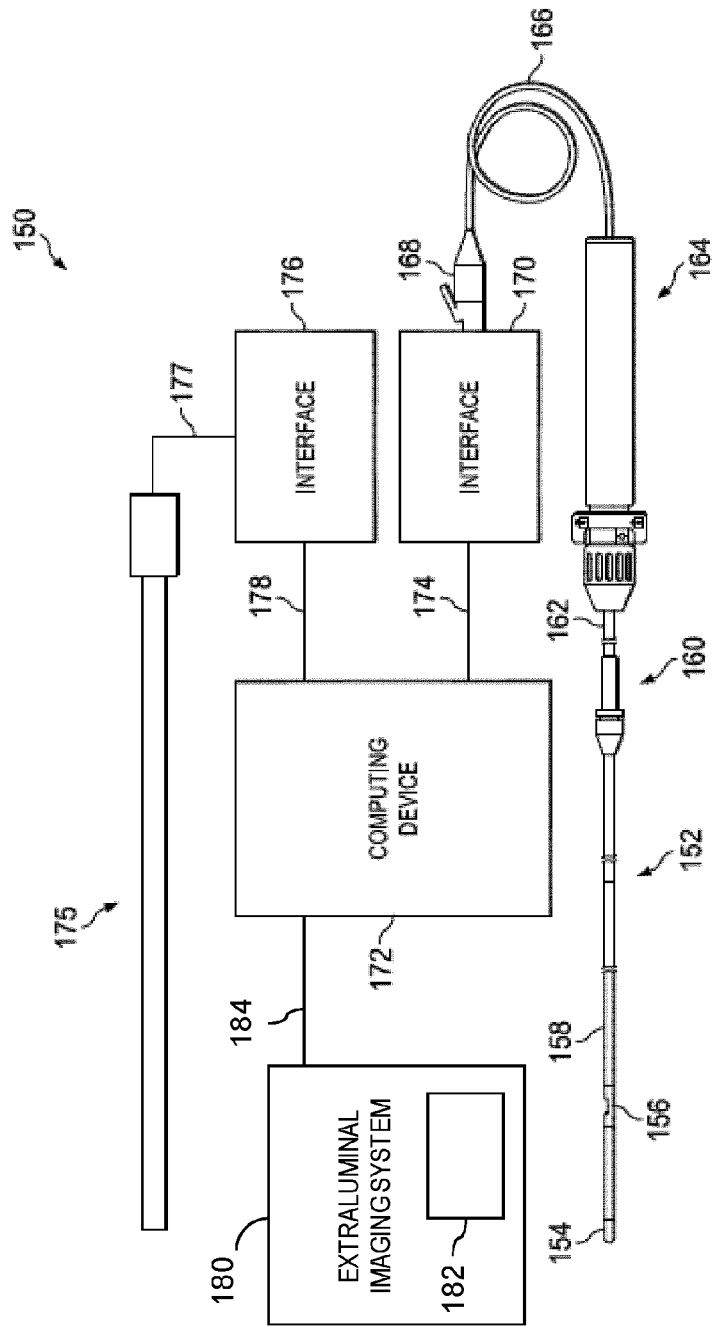
FIG. 4A shows a diagrammatic, schematic view of an intraluminal imaging system with pressure guide wire according to an embodiment of the present disclosure.
Figure 4B:
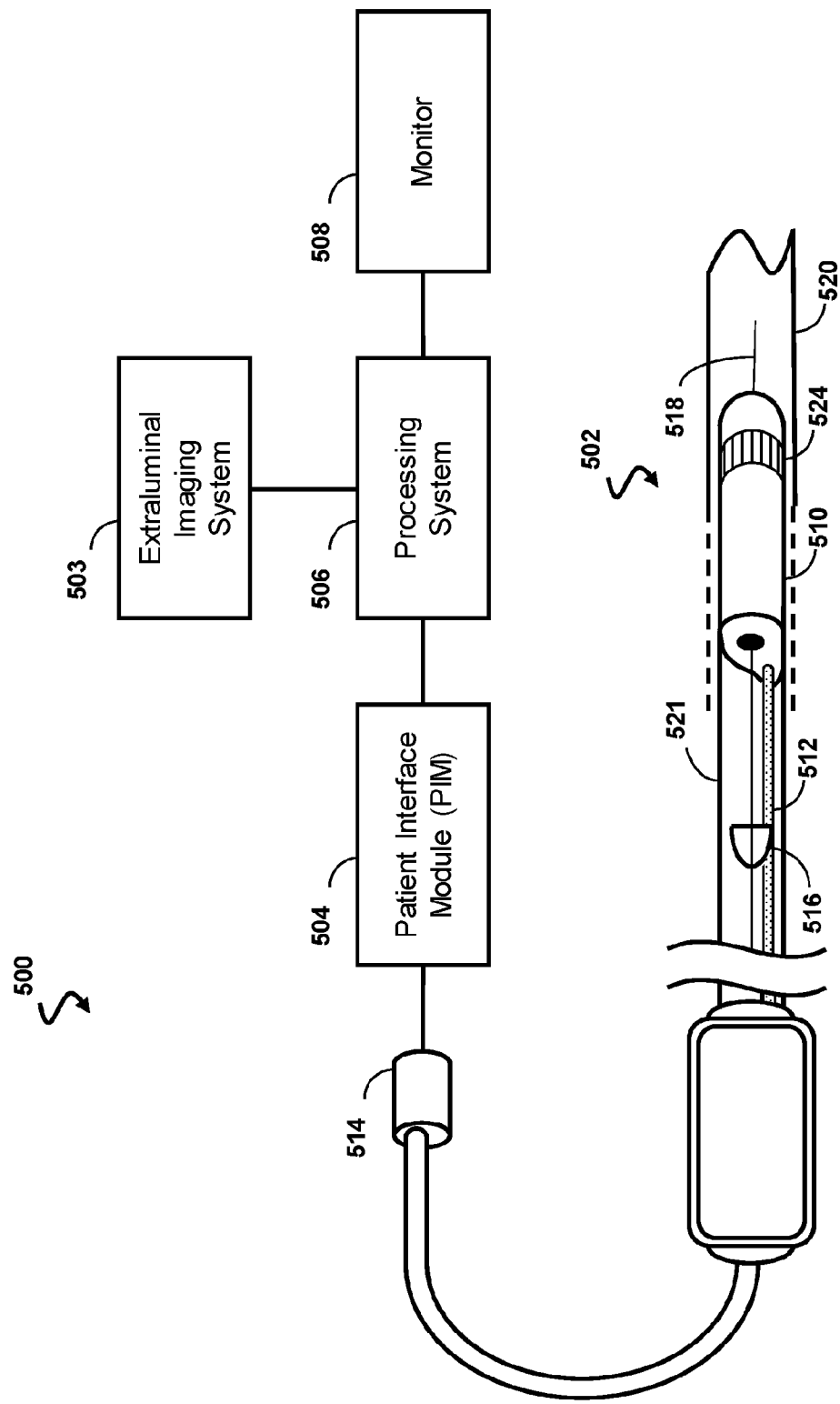
FIG. 4B shows a diagrammatic, schematic view of an intravascular ultrasound (IVUS) imaging system according to an embodiment of the present disclosure.

Referring now to FIG. 4A, shown therein is a system 150 according to an embodiment of the present disclosure. In that regard, FIG. 4A is a diagrammatic, schematic view of the system 150. As shown, the system 150 includes an instrument 152. In that regard, in some instances instrument 152 is suitable for use as at least one of instruments 130 and 132 discussed above. Accordingly, in some instances the instrument 152 includes features similar to those discussed above with respect to instruments 130 and 132 in some instances. In the illustrated embodiment, the instrument 152 is a guide wire having a distal portion 154 and a housing 156 positioned adjacent the distal portion. In that regard, the housing 156 is spaced approximately 3 cm from a distal tip of the instrument 152. The housing 156 is configured to house one or more sensors, transducers, and/or other monitoring elements configured to obtain the diagnostic information about the vessel. In the illustrated embodiment, the housing 156 contains at least a pressure sensor configured to monitor a pressure within a lumen in which the instrument 152 is positioned. A shaft 158 extends proximally from the housing 156. A torque device 160 is positioned over and coupled to a proximal portion of the shaft 158. A proximal end portion 162 of the instrument 152 is coupled to a connector 164. A cable 166 extends from connector 164 to a connector 168. In some instances, connector 168 is configured to be plugged into an interface 170. In that regard, interface 170 can be a patient interface module (PIM). In some instances, the cable 166 is replaced with a wireless connection. In that regard, it is understood that various communication pathways between the instrument 152 and the interface 170 may be utilized, including physical connections (including electrical, optical, and/or fluid connections), wireless connections, and/or combinations thereof.

The interface 170 is communicatively coupled to a computing device 172 via a connection 174. Computing device 172 is generally representative of any device suitable for performing the processing and analysis techniques discussed within the present disclosure. In some embodiments, the computing device 172 includes a processor, random access memory, and a storage medium. In that regard, in some particular instances the computing device 172 is programmed to execute steps associated with the data acquisition and analysis described herein. Accordingly, it is understood that any steps related to data acquisition, data processing, instrument control, and/or other processing or control aspects of the present disclosure may be implemented by the computing device using corresponding instructions stored on or in a non-transitory computer readable medium accessible by the computing device. In some instances, the computing device 172 is a console device. In some particular instances, the computing device 172 is similar to the s5™ Imaging System or the s5i™ Imaging System, each available from Volcano Corporation, or the CORE, CORE MOBILE, CORE M2, or IntraSight systems available from Koninklijke Philips, N.V. In some instances, the computing device 172 is portable (e.g., handheld, on a rolling cart, etc.). Further, it is understood that in some instances the computing device 172 comprises a plurality of computing devices. In that regard, it is particularly understood that the different processing and/or control aspects of the present disclosure may be implemented separately or within predefined groupings using a plurality of computing devices. For example, in some embodiments, the computing device 172 comprises two distinct computing components or devices in communication with one another. Any divisions and/or combinations of the processing and/or control aspects described below across multiple computing devices are within the scope of the present disclosure.

Together, connector 164, cable 166, connector 168, interface 170, and connection 174 facilitate communication between the one or more sensors, transducers, and/or other monitoring elements of the instrument 152 and the computing device 172. However, this communication pathway is exemplary in nature and should not be considered limiting in any way. In that regard, it is understood that any communication pathway between the instrument 152 and the computing device 172 may be utilized, including physical connections (including electrical, optical, and/or fluid connections), wireless connections, and/or combinations thereof. In that regard, it is understood that the connection 174 is wireless in some instances. In some instances, the connection 174 includes a communication link over a network (e.g., intranet, internet, telecommunications network, and/or other network). In that regard, it is understood that the computing device 172 is positioned remote from an operating area where the instrument 152 is being used in some instances. Having the connection 174 include a connection over a network can facilitate communication between the instrument 152 and the remote computing device 172 regardless of whether the computing device is in an adjacent room, an adjacent building, or in a different state/country. Further, it is understood that the communication pathway between the instrument 152 and the computing device 172 is a secure connection in some instances. Further still, it is understood that, in some instances, the data communicated over one or more portions of the communication pathway between the instrument 152 and the computing device 172 is encrypted.

The system 150 also includes an instrument 175. In that regard, in some instances instrument 175 is suitable for use as at least one of instruments 130 and 132 discussed above. Accordingly, in some instances the instrument 175 includes features similar to those discussed above with respect to instruments 130 and 132 in some instances. In the illustrated embodiment, the instrument 175 is a catheter-type device. In that regard, the instrument 175 includes one or more sensors, transducers, and/or other monitoring elements adjacent a distal portion of the instrument configured to obtain the diagnostic information about the vessel. In the illustrated embodiment, the instrument 175 includes a pressure sensor configured to monitor a pressure within a lumen in which the instrument 175 is positioned. The instrument 175 is in communication with an interface 176 via connection 177. In some instances, interface 176 is a hemodynamic monitoring system or other control device, such as Siemens AXIOM Sensis, Mennen Horizon XVu, and Philips Xper IM Physiomonitoring 5. In one particular embodiment, instrument 175 is a pressure-sensing catheter that includes fluid column extending along its length. In such an embodiment, interface 176 includes a hemostasis valve fluidly coupled to the fluid column of the catheter, a manifold fluidly coupled to the hemostasis valve, and tubing extending between the components as necessary to fluidly couple the components. In that regard, the fluid column of the catheter is in fluid communication with a pressure sensor via the valve, manifold, and tubing. In some instances, the pressure sensor is part of interface 176. In other instances, the pressure sensor is a separate component positioned between the instrument 175 and the interface 176. The interface 176 is communicatively coupled to the computing device 172 via a connection 178.

Similar to the connections between instrument 152 and the computing device 172, interface 176 and connections 177 and 178 facilitate communication between the one or more sensors, transducers, and/or other monitoring elements of the instrument 175 and the computing device 172. However, this communication pathway is exemplary in nature and should not be considered limiting in any way. In that regard, it is understood that any communication pathway between the instrument 175 and the computing device 172 may be utilized, including physical connections (including electrical, optical, and/or fluid connections), wireless connections, and/or combinations thereof. In that regard, it is understood that the connection 178 is wireless in some instances. In some instances, the connection 178 includes a communication link over a network (e.g., intranet, internet, telecommunications network, and/or other network). In that regard, it is understood that the computing device 172 is positioned remote from an operating area where the instrument 175 is being used in some instances. Having the connection 178 include a connection over a network can facilitate communication between the instrument 175 and the remote computing device 172 regardless of whether the computing device is in an adjacent room, an adjacent building, or in a different state/country. Further, it is understood that the communication pathway between the instrument 175 and the computing device 172 is a secure connection in some instances. Further still, it is understood that, in some instances, the data communicated over one or more portions of the communication pathway between the instrument 175 and the computing device 172 is encrypted.

The computing device 172 is also in communication with an extraluminal imaging system 180 that obtains extraluminal images of a body lumen. The extraluminal imaging system 180 is in communication with the computing device 172 via a communication link 184, which may be wireless or wired as similarly described above. In some embodiments, the extraluminal imaging system 180 includes an imaging device 182 and/or processing hardware and software to control operation of the imaging device and/or generate the extraluminal image. The extraluminal imaging system 180 can be an extravascular imaging system that obtains extravascular imagines of a blood vessel. In some embodiments, the computing device 172 is contained within a single housing. The single housing can include processing hardware and software associated with both intravascular data and extravascular imaging. In some embodiments, the computing device 172 includes multiple housings in communication with one another. One housing can include processing hardware and software associated with intravascular data. Another housing can include processing hardware and software associated with extravascular imaging. In such instances, a processing system can be associated with intravascular data, and another processing system can be associated with extravascular imaging.

The computing device 172 receives extravascular images from the extravascular imaging system 180. The extravascular imaging device 182 can obtain images of the body lumen while positioned outside of the patient's body. The computing device 172 can generate extravascular images from data obtained by the extravascular imaging device 182. For example, the computing device 172 can receive and process electrical signals from the extravascular imaging device 182 that are representative of the anatomy in the extravascular image and output an extravascular image. In some instances, the extravascular imaging device 182 and/or a processing system associated with the extravascular imaging device 182 generates the extravascular images and transmits the extravascular images to the computing device 172. Examples of extravascular imaging devices include external ultrasound, x-ray, angiography, fluoroscopy, computed tomography (CT), and/or magnetic resonance imaging (MRI) devices. Angiography or arteriography imaging technique is used to visualize the inside of a lumen in blood vessels and other organs of the body, with particular interest in the arteries, veins, and the heart chambers. This is traditionally done by injecting a radio-opaque contrast agent into the blood vessel and imaging using x-ray based techniques. Angiogram is an image of the vessel with contrast media such that the contour of the vessel is visible in the x-ray image. For example, angiography can be any suitable type, including digital subtraction angiography. Fluoroscopy uses x-rays to obtain real-time moving images of the interior of a vessel. In some instances, fluoroscopy is performed without injection of the contrast agent. One or more these techniques allow the interventional radiologist or cardiologist to see stenosis (blockages or narrowing) inside the vessel which may be inhibiting the flow of blood and causing pain.

It is understood that one or more components of the system 150 are not included, are implemented in a different arrangement/order, and/or are replaced with an alternative device/mechanism in other embodiments of the present disclosure. For example, in some instances, the system 150 does not include interface 170 and/or interface 176. In such instances, the connector 168 (or other similar connector in communication with instrument 152 or instrument 175) may plug into a port associated with computing device 172. Alternatively, the instruments 152, 175 may communicate wirelessly with the computing device 172. Generally speaking, the communication pathway between either or both of the instruments 152, 175 and the computing device 172 may have no intermediate nodes (i.e., a direct connection), one intermediate node between the instrument and the computing device, or a plurality of intermediate nodes between the instrument and the computing device.

FIG. 4B is a diagrammatic schematic view of an ultrasound imaging system 500, according to aspects of the present disclosure. The ultrasound imaging system 500 can be an intraluminal imaging system. In some instances, the system 500 can be an intravascular ultrasound (IVUS) imaging system. The system 500 may include an intraluminal imaging device 502 such as a catheter, guide wire, or guide catheter, a patient interface module (PIM) 504, a processing system or console 506, an extraluminal imaging system 503, and a monitor 508. The intraluminal imaging device 502 can be an ultrasound imaging device. In some instances, the device 502 can be IVUS imaging device, such as a solid-state IVUS device.

At a high level, the IVUS device 502 emits ultrasonic energy, or ultrasound signals, from a transducer or transducer array 524 included in scanner assembly 510 mounted near a distal end of the catheter device 502. In some embodiments, the transducer or transducer array comprises a single transducer element. In other embodiments, the transducer array comprises multiple transducer elements. The ultrasonic energy is reflected by tissue structures in the medium, such as a vessel 520, or another body lumen surrounding the scanner assembly 510, and the ultrasound echo signals are received by the transducer array 524. In that regard, the device 502 can be sized, shaped, or otherwise configured to be positioned within the body lumen of a patient. The PIM 504 transfers the received echo signals to the console or computer 506 where the ultrasound image (including the flow information) is reconstructed and displayed on the monitor 508. The console or computer 506 can include a processor and a memory. The computer or computing device 506 can be operable to facilitate the features of the IVUS imaging system 500 described herein. For example, the processor can execute computer readable instructions stored on the non-transitory tangible computer readable medium.

The PIM 504 facilitates communication of signals between the IVUS console 506 and the scanner assembly 510 included in the IVUS device 502. This communication includes the steps of: (1) providing commands to integrated circuit controller chip(s) included in the scanner assembly 510 to select the particular transducer array element(s), or acoustic element(s), to be used for transmit and receive, (2) providing the transmit trigger signals to the integrated circuit controller chip(s) included in the scanner assembly 510 to activate the transmitter circuitry to generate an electrical pulse to excite the selected transducer array element(s), and/or (3) accepting amplified echo signals received from the selected transducer array element(s) via amplifiers included on the integrated circuit controller chip(s) of the scanner assembly 510. In some embodiments, the PIM 504 performs preliminary processing of the echo data prior to relaying the data to the console 506. In examples of such embodiments, the PIM 504 performs amplification, filtering, and/or aggregating of the data. In an embodiment, the PIM 504 also supplies high- and low-voltage DC power to support operation of the device 502 including circuitry within the scanner assembly 510.

The IVUS console 506 receives the echo data from the scanner assembly 510 by way of the PIM 504 and processes the data to reconstruct an image of the tissue structures in the medium surrounding the scanner assembly 510. The console 506 outputs image data such that an image of the vessel 520, such as a cross-sectional image of the vessel 520, is displayed on the monitor 508. Vessel 520 may represent fluid filled or surrounded structures, both natural and man-made. The vessel 520 may be within a body of a patient. The vessel 520 may be a blood vessel, as an artery or a vein of a patient's vascular system, including cardiac vasculature, peripheral vasculature, neural vasculature, renal vasculature, and/or or any other suitable lumen inside the body. For example, the device 502 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 502 may be used to examine man-made structures such as, but without limitation, heart valves, stents, shunts, filters and other devices.

The processing system 506 is also in communication with an extraluminal imaging system 503 that obtains extraluminal images of a body lumen. The extraluminal imaging system 503 is in communication with the processing system 506 via a communication link, which may be wireless or wired as similarly described above. In some embodiments, the extraluminal imaging system 503 includes an imaging device and/or processing hardware and software to control operation of the imaging device and/or generate the extraluminal image. The extraluminal imaging system 503 can be an extravascular imaging system that obtains extravascular imagines of a blood vessel. In some embodiments, the processing system 506 is contained within a single housing. The single housing can include processing hardware and software associated with both intravascular data and extravascular imaging. In some embodiments, the processing system 506 includes multiple housings in communication with one another. One housing can include processing hardware and software associated with intravascular data. Another housing can include processing hardware and software associated with extravascular imaging. In such instances, a processing system can be associated with intravascular data, and another processing system can be associated with extravascular imaging.

The processing system 506 receives extravascular images from the extravascular imaging system 503. The extravascular imaging device can obtain images of the body lumen while positioned outside of the patient's body. The processing system 506 can generate extravascular images from data obtained by the extravascular imaging device. For example, the processing system 506 can receive and process electrical signals from the extravascular imaging device that are representative of the anatomy in the extravascular image and output an extravascular image. In some instances, the extravascular imaging device generates the extravascular images and transmits the extravascular images to the processing system 506. Examples of extravascular imaging devices include external ultrasound, x-ray, angiography, fluoroscopy, computed tomography (CT), and/or magnetic resonance imaging (MRI) devices. Angiography or arteriography imaging technique is used to visualize the inside of a lumen in blood vessels and other organs of the body, with particular interest in the arteries, veins, and the heart chambers. This is traditionally done by injecting a radio-opaque contrast agent into the blood vessel and imaging using x-ray based techniques. Angiogram is an image of the vessel with contrast media such that the contour of the vessel is visible in the x-ray image. For example, angiography can be any suitable type, including digital subtraction angiography. Fluoroscopy uses x-rays to obtain real-time moving images of the interior of a vessel. In some instances, fluoroscopy is performed without injection of the contrast agent. One or more these techniques allow the interventional radiologist or cardiologist to see stenosis (blockages or narrowing) inside the vessel which may be inhibiting the flow of blood and causing pain.

In some embodiments, the IVUS device includes some features similar to traditional solid-state IVUS catheters, such as the EagleEye® catheter available from Koninklijke Philips N.V. and those disclosed in U.S. Pat. No. 7,846,101 hereby incorporated by reference in its entirety. For example, the IVUS device 502 includes the scanner assembly 510 near a distal end of the device 502 and a transmission line bundle 512 extending along the longitudinal body of the device 502. The transmission line bundle or cable 512 can include a plurality of conductors, including one, two, three, four, five, six, seven, or more conductors. It is understood that any suitable gauge wire can be used for the conductors. In an embodiment, the cable 512 can include a four-conductor transmission line arrangement with, e.g., 41 American Wire Gauge (AWG) wires. In an embodiment, the cable 512 can include a seven-conductor transmission line arrangement utilizing, e.g., 44 AWG wires. In some embodiments, 43 AWG wires can be used.

The transmission line bundle 512 terminates in a PIM connector 514 at a proximal end of the device 502. The PIM connector 514 electrically couples the transmission line bundle 512 to the PIM 504 and physically couples the IVUS device 502 to the PIM 504. In an embodiment, the IVUS device 502 further includes a guide wire exit port 516. Accordingly, in some instances the IVUS device is a rapid-exchange catheter. The guide wire exit port 516 allows a guide wire 518 to be inserted towards the distal end in order to direct the device 502 through the vessel 520.

In an embodiment, the processing system 506 generates flow data by processing the echo signals from the IVUS device 502 into Doppler power or velocity information. The processing system 506 may also generate B-mode data by applying envelope detection and logarithmic compression on the conditioned echo signals. The processing system 506 can further generate images in various views, such as 2D and/or 3D views, based on the flow data or the B-mode data. The processing system 506 can also perform various analyses and/or assessments. For example, the processing system 506 can apply virtual histology (VH) techniques, for example, to analyze or assess plaques within a vessel (e.g., the vessel 520). The images can be generated to display a reconstructed color-coded tissue map of plaque composition superimposed on a cross-sectional view of the vessel.

In an embodiment, the processing system 506 can apply a blood flow detection algorithm (e.g., ChromaFlo) to determine the movement of blood flow, for example, by acquiring image data of a target region (e.g., the vessel 520) repeatedly and determining the movement of the blood flow from the image data. The blood flow detection algorithm operates based on the principle that signals measured from vascular tissue are relatively static from acquisition to acquisition, whereas signals measured from blood flow vary at a characteristic rate corresponding to the flow rate. As such, the blood flow detection algorithm may determine movements of blood flow based on variations in signals measured from the target region between repeated acquisitions. To acquire the image data repeatedly, the processing system 506 may control to the device 502 to transmit repeated pulses on the same aperture.

While the present disclosure describes embodiments related to intravascular ultrasound (IVUS) imaging using an intravascular catheter or guidewire, it is understood that one or more aspects of the present disclosure can be implemented in any suitable ultrasound imaging system, including a synthetic aperture ultrasound imaging system, a phased array ultrasound imaging system, or any other array-based ultrasound imaging system. For example, aspects of the present disclosure can be implemented in intraluminal ultrasound imaging systems using an intracardiac (ICE) echocardiography catheter and/or a transesophageal echocardiography (TEE) probe, and/or external ultrasound imaging system using an ultrasound probe configured for imaging while positioned adjacent to and/or in contact with the patient's skin. The ultrasound imaging device can be a transthoracic echocardiography (TTE) imaging device in some embodiments.

An ultrasound transducer array of ultrasound imaging device includes an array of acoustic elements configured to emit ultrasound energy and receive echoes corresponding to the emitted ultrasound energy. In some instances, the array may include any number of ultrasound transducer elements. For example, the array can include between 2 acoustic elements and 100,000 acoustic elements, including values such as 2 acoustic elements, 4 acoustic elements, acoustic elements, 64 acoustic elements, 128 acoustic elements, 500 acoustic elements, 812 acoustic elements, 3,000 acoustic elements, 10,000 acoustic elements, 20,000 acoustic elements, 50,000 acoustic elements, 65,000 acoustic elements, and/or other values both larger and smaller. In some instances, the transducer elements of the array may be arranged in any suitable configuration, such as a linear array, a planar array, a curved array, a curvilinear array, a circumferential array, an annular array, a phased array, a matrix array, a one-dimensional (1D) array, a 1.x dimensional array (e.g., a 1.5D array), or a two-dimensional (2D) array. The array of transducer elements (e.g., one or more rows, one or more columns, and/or one or more orientations) can be uniformly or independently controlled and activated. The array can be configured to obtain one-dimensional, two-dimensional, and/or three-dimensional images of patient anatomy.

The ultrasound transducer elements may include piezoelectric/piezoresistive elements, piezoelectric micromachined ultrasound transducer (PMUT) elements, capacitive micromachined ultrasound transducer (CMUT) elements, and/or any other suitable type of ultrasound transducer elements. The ultrasound transducer elements of the array are in communication with (e.g., electrically coupled to) electronic circuitry. For example, the electronic circuitry can include one or more transducer control logic dies. The electronic circuitry can include one or more integrated circuits (IC), such as application specific integrated circuits (ASICs). In some embodiments, one or more of the ICs can include a microbeamformer (pBF). In other embodiments, one or more of the ICs includes a multiplexer circuit (MUX).

Figure 5:
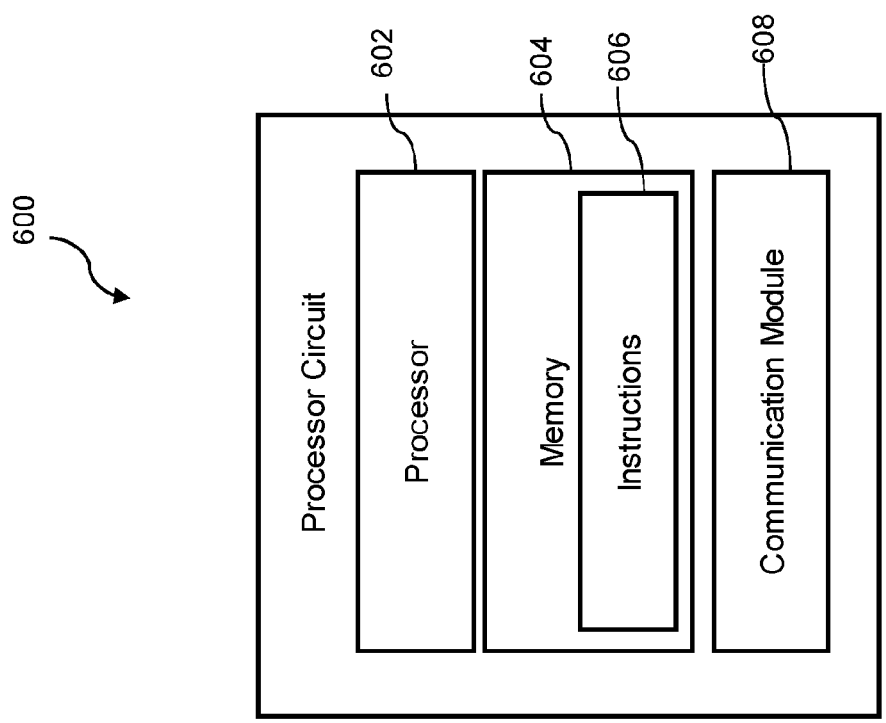
FIG. 5 is a diagrammatic schematic view of a processor circuit, according to embodiments of the present disclosure.

FIG. 5 is a schematic diagram of a processor circuit 600, according to embodiments of the present disclosure. The processor circuit 600 may be implemented in the computing device 172, interfaces 170 and 176, the intraluminal device 152, and/or the extraluminal imaging system 175 shown in FIG. 4A, or the processing system 506 or extraluminal imaging system 506 shown in FIG. 4B. As shown, the processor circuit 600 may include a processor 602, a memory 604, and a communication module 608. These elements may be in direct or indirect communication with each other, for example via one or more buses.

The processor 602 may include a central processing unit (CPU), a digital signal processor (DSP), an ASIC, a controller, an FPGA, another hardware device, a firmware device, or any combination thereof configured to perform the operations described herein. The processor 602 may also be implemented as a combination of computing devices, e.g., a combination of a DSP and a microprocessor, a plurality of microprocessors, one or more microprocessors in conjunction with a DSP core, or any other such configuration.

The memory 604 may include a cache memory (e.g., a cache memory of the processor 602), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 604 includes a non-transitory computer-readable medium. The memory 604 may store instructions 606. The instructions 606 may include instructions that, when executed by the processor 602, cause the processor 602 to perform the operations described herein with reference to the computing device 172, extraluminal imaging system 180, and/or intraluminal device 152 shown in FIG. 4A, or the processing system 506, intraluminal device 502, or extraluminal imaging system 503 of FIG. 4B. Instructions 606 may also be referred to as code. The terms "instructions" and "code" should be interpreted broadly to include any type of computer-readable statement(s). For example, the terms "instructions" and "code" may refer to one or more programs, routines, subroutines, functions, procedures, etc. "Instructions" and "code" may include a single computer-readable statement or many computer-readable statements.

The communication module 608 can include any electronic circuitry and/or logic circuitry to facilitate direct or indirect communication of data between processor circuit 600, and the computing device 172, the intraluminal device 152, or the processing system 506, the imaging device 502, and/or the monitor 508. In that regard, the communication module 608 can be an input/output (I/O) device. In some instances, the communication module 608 facilitates direct or indirect communication between various elements of the processor circuit 600 and/or the components of the systems shown in FIGS. 4A and 4B.

Figure 6:
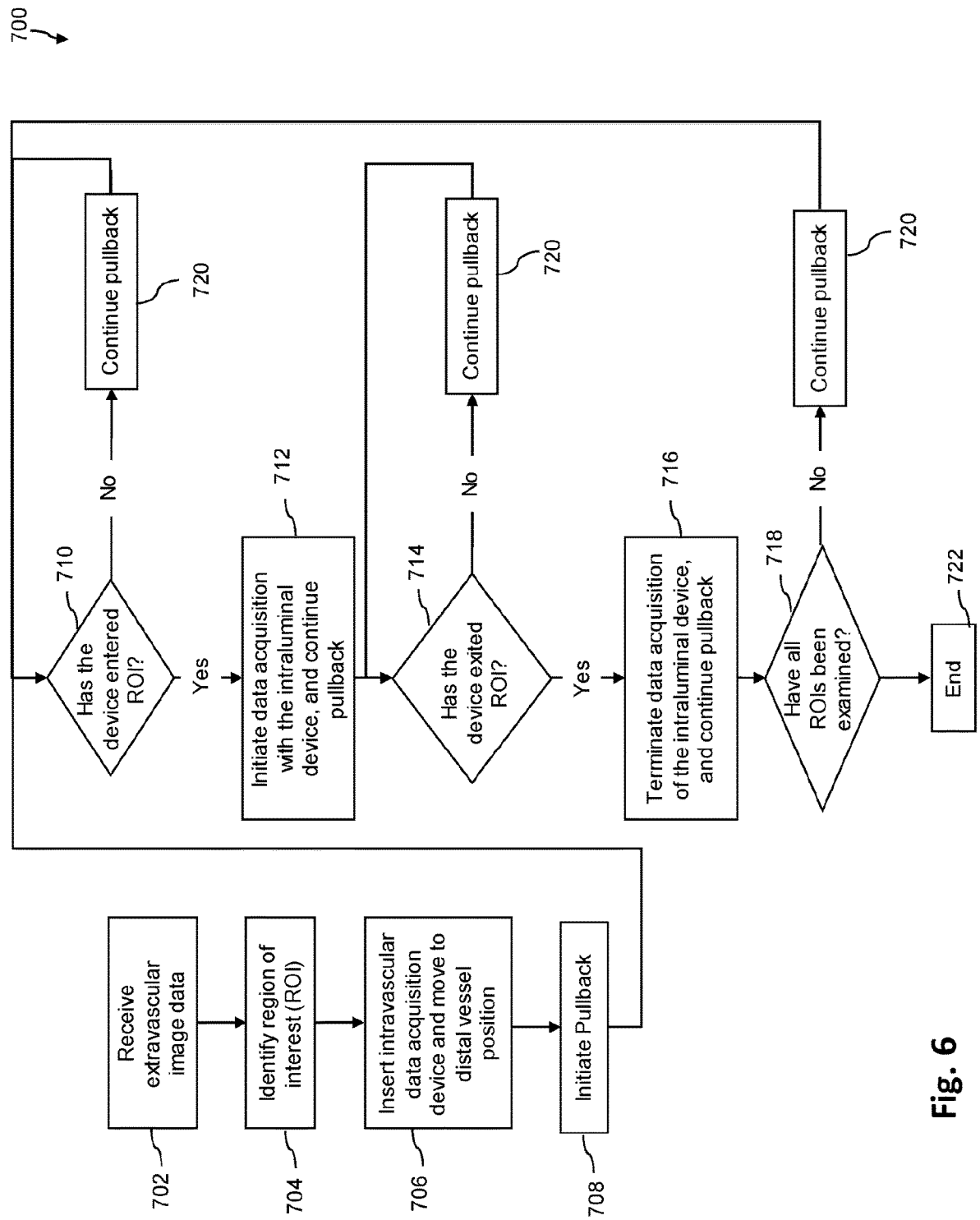
FIG. 6 is a decision-flow diagram of an automated method for acquisition of intraluminal data, according to embodiments of the present disclosure.

FIG. 6 is a flow diagram of a method for controlling acquisition of intraluminal data, according to embodiments of the present disclosure. The decision method 700 includes exemplary steps that may simplify the workflow in the characterization lab by automating part of the data acquisition process. In some embodiments, the steps of the method 700 may be carried out by one or more of the components of the instruments explained in FIGS. 3, 4A and 4B and/or the processor circuit 600 shown in FIG. 5. It is understood that the steps of method 700 may be performed in a different order than shown in FIG. 6, that additional steps can be provided before, during, and after the steps, and/or some of the steps described can be replaced or eliminated in other embodiments. Step 702, a processor circuit receives extravascular image data, such as angiographic image data, that represents vasculature of the patient. In some embodiments, the processor circuit may receive the extravascular image data from an extravascular imaging device, such as an x-ray imaging device, a computed tomography (CT) device, or any other suitable imaging device. For example, the extravascular image data may comprise one or more angiographic image frames in which a contrast agent has been introduced into the patient's vasculature. In some embodiments, the processor circuit receives a plurality of extravascular image frames obtained at a respective plurality of times. For example, the plurality of extravascular image frames may represent the vasculature at various times during cyclical movement of the patient due to a heart beat, breathing, etc. Accordingly, the processor circuit may identify or designate one of the image frames as a roadmap image based on various parameters of the frame, including contrast, intensity, amount of contrast agent, etc. Further, the processor circuit may identify or designate a roadmap for a plurality of different points in time during the patient's cyclical movement (e.g., heart beat, breathing). In some embodiments, once a roadmap image has been designated, the processor circuit performs image processing on the roadmap image to identify vessels in the image. For example, the processor circuit may be configured to perform segmentation, QCA, or any other suitable image processing technique to identify vascular shapes and pathways in the roadmap image.

At step 704, the processor circuit identifies a region of interest (ROI) of a vessel. In some embodiments, the processor circuit identifies or designates the ROI based on input received from a user input device. For example, a user may use a mouse, trackball, trackpad, keyboard, or any suitable peripheral interface device to select a region of the vasculature. In some embodiments, the user interface device comprises a touch screen display, and the user enters the input to select the region of interest by touching a location or area on the screen. In some embodiments, the user input identifies a proximal point and a distal point on a vessel, and the processor circuit identifies the length of the vessel between the proximal point and the distal point as the ROI. In some embodiments, the user traces a length of the vessel to identify the ROI on a touch screen display. Further, it will be understood that the processor circuit can be configured to receive multiple inputs corresponding to multiple ROIs. For example, a first ROI may be identified by a first user input associated with a first location of a vessel, and a second ROI may be identified by a second user input associated with a second location of the vessel. In some embodiments, the first and second ROI may correspond to different vessels or branches of the vasculature.

In other embodiments, the processor circuit is configured to automatically identify one or more ROIs. For example, based on image processing (e.g., segmentation, QCA), the processor circuit may identify vessels that are at higher risk due to lesions or stenoses. In some embodiments, the processor circuit may evaluate vessel diameters or cross-sectional areas at a plurality of locations to identify narrowed regions of a vessel that may include stenoses or lesions. The processor circuit may then designate one or more ROIs corresponding to the identified stenoses. For example, the processor circuit may designate an ROI as a length of the vessel that includes a stenosis.

Step 706, the intravascular data acquisition device is inserted into the vasculature of the patient. The intravascular data acquisition device may be configured for the acquisition of one or more types of data of the vessel, such as pressure data, flow data, temperature data, and/or image data. For example, the intravascular data acquisition device may comprise one or more of a pressure-sensing guidewire, a pressure-sensing catheter, a flow-sensing guidewire, a flow-sensing catheter, a temperature sensor, and IVUS imaging catheter, an OCT imaging catheter, a FLIVUS imaging device, or any other suitable type of device. The device may include a sensor coupled to a distal end of a flexible elongate member configured to be positioned within the vasculature of a patient. In that regard, the device may include one or more of the devices shown in FIG. 4A, for example, including the instrument 175 and/or the instrument 152.

The device may be inserted under extravascular imaging, such as external ultrasound, fluoroscopic imaging, angiographic imaging or any other suitable extravascular imaging modality. For example, the processor circuit may be configured to receive second extravascular imaging data of the vessel and the intravascular data acquisition device. The processor circuit may then co-register the second extravascular image data (e.g., fluoroscopic image data) to the roadmap to provide image-based guidance for the intravascular data acquisition procedure. In some embodiments, the intravascular data acquisition device includes one or more markers that are visible in the second extravascular image data. In some embodiments, the processor circuit is configured to provide a screen display to a physician that includes the roadmap image and an indicator of the intravascular data acquisition device's position in the vessel. In some embodiments, the screen display comprises an overlay of a current fluoroscopic image on the roadmap image. The screen display may be continuously updated such that a current or real-time position of the marker of the intravascular data acquisition device is shown at the corresponding location in the roadmap image. In some embodiments, the processor circuit is configured to generate a graphical representation of the intravascular imaging device based on the second extravascular image data. The processor circuit may then generate the screen display to include the graphical representation positioned at a corresponding position on the roadmap image. In some embodiments, the screen display comprises an additional graphical representation of the region of interest identified in step 704.

At step 708, a pullback procedure is initiated. In some embodiments, the pullback is performed manually by the physician. For example, the physician may manually retract or pull the intravascular data acquisition device in a proximal direction. In some embodiments, the pullback is initiated by the physician but controlled automatically by a mechanical actuator, such as an electrical motor. During the pullback procedure, the processor circuit may track the location of the intraluminal device within the vasculature using the second extravascular image data. For example, the location of the intravascular data acquisition device may be tracked using co-registered fluoroscopic image data.

In step 710, the processor circuit determines, based on the tracked location of the intravascular data acquisition device, whether the device has entered the ROI. In some embodiments, step 710 includes comparing, with respect to the roadmap, the location of the device relative to the ROI. In some embodiments, tracking the location of the device includes mapping the current location of the device to a location of a vessel segment. For example, in some embodiments, a center line of the vessel is determined using a vessel segmentation technique, and the current location of the device is mapped to the nearest point on the center line. If the device has entered the ROI, the processor circuit automatically begins receiving intravascular data in step 712. In some embodiments, step 712 includes causing the intravascular data acquisition device to begin acquiring intravascular data, such as pressure data, flow data, IVUS data, OCT data, or any other suitable type of intravascular data. In some embodiments, the intravascular data acquisition device is already acquiring data, and the processor circuit causes the data to be stored to a memory in response to determining that the device has entered the ROI. In some embodiments, the intravascular data is being acquired and saved to memory before the intravascular device enters the ROI, and the processor circuit is configured to generate a time stamp indicating when the intravascular data acquisition device enters the ROI. The time stamp may then be used to identify intravascular data that corresponds to the ROI, and to exclude intravascular data that does not correspond to the ROI. Referring again to step 710, if the processor instead determines that the intravascular data acquisition device has not entered the ROI, step 710 is repeated in a looped fashion while the pullback continues until the processor circuit determines that the device has entered the ROI.

In step 714, the processor circuit determines whether the intravascular data acquisition device has exited the ROI. In some embodiments, the processor circuit may determine whether the device has exited the ROI in a similar fashion used to determine whether the device has entered the ROI. If the device has exited the ROI, the processor circuit automatically ceases receiving intravascular data in step 716. In some embodiments, step 716 includes causing the data to stop being stored to the memory in response to determining that the device has exited the ROI. In some embodiments, step 716 includes generating a time stamp indicating when the intravascular data acquisition device exits the ROI. The time stamp may then be used with the earlier time stamp generated when the device entered to ROI to identify intravascular data that corresponds to the ROI, and to exclude intravascular data that does not correspond to the ROI. Referring again to step 714, if the processor instead determines that the intravascular data acquisition device has not exited the ROI, step 714 is repeated in a looped fashion while the pullback continues until the processor circuit determines that the device has exited the ROI.

In step 718, the processor circuit determines whether intravascular data has been acquired for all identified ROIs. As mentioned above, in some embodiments, the processor circuit identifies multiple ROIs corresponding to different segments of a same vessel and/or segments of different vessels. In an exemplary embodiment in which multiple ROIs are identified on a single vessel or vessel branch, once the processor circuit determines that the intravascular data acquisition device has obtained data of an ROI and exited the ROI, the processor circuit may then determine if there are other ROIs that have not already been examined. If all ROIs have been examined, the intraluminal data acquisition procedure is terminated in step 722. If, on the other hand, the processor circuit determines that there are other ROIs on the vessel that have not yet been examined, the processor circuit continues the pullback procedure and repeats the portion of the method 700 starting with step 710.

Figure 7:
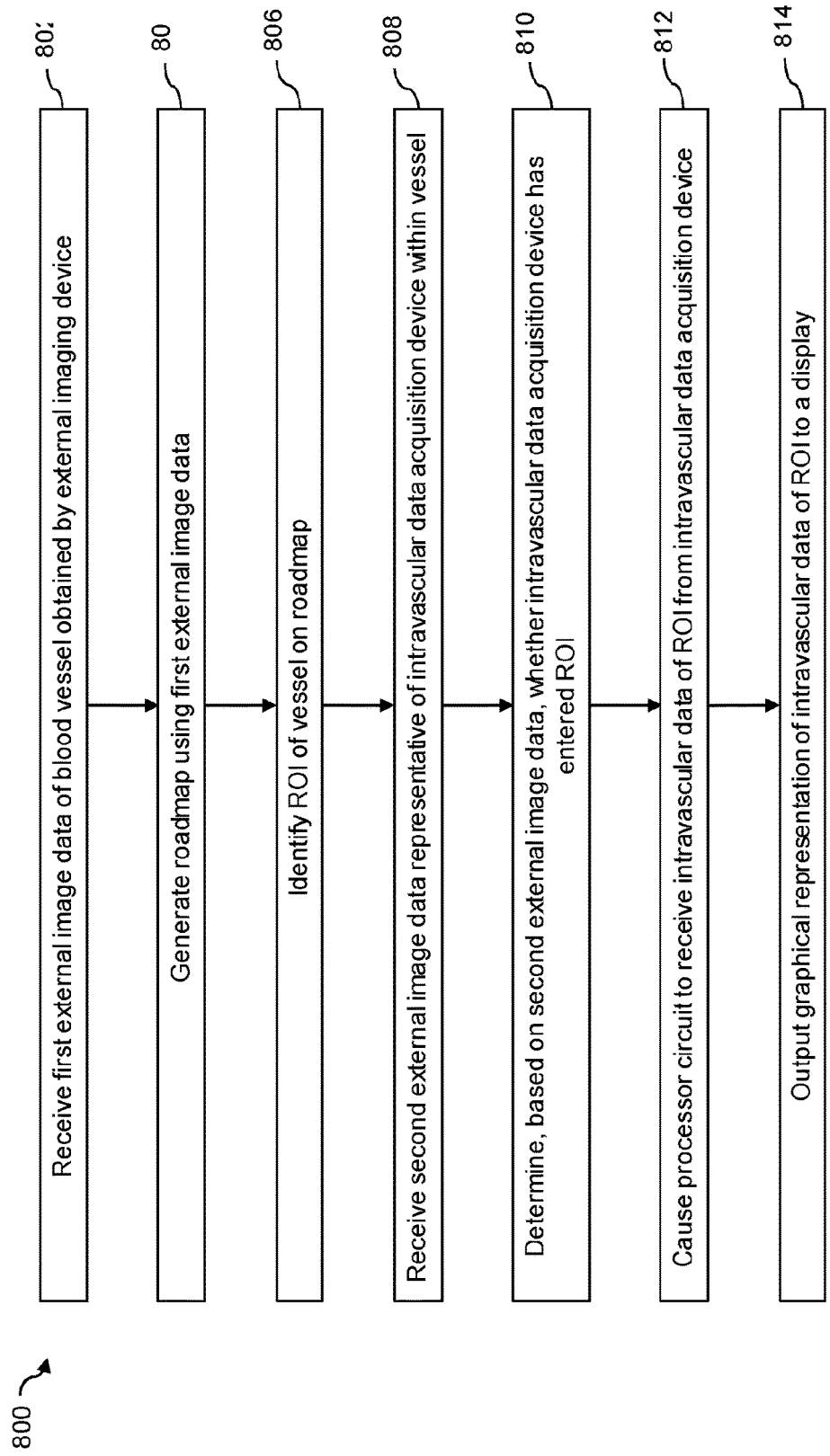
FIG. 7 is a flow diagram showing method steps of a processor executing the automated acquisition of intraluminal data, according to embodiments of the present disclosure

FIG. 7 is a flow diagram illustrating a method 800 for controlling intravascular data acquisition. It will be understood that the method 800 may be performed using one or more of the devices and/or systems described above, including the system 150, 132, and/or the processor circuit 600.

In step 802, a processor circuit receives first external image data of a blood vessel, such as an extravascular image generated by an extravascular imaging device (e.g., FIG. 4A (175)). In some embodiments, the first external image data comprises one or more angiographic images. In some embodiments, the first external image data includes 2D image data and/or 3D image data of the vessel. The first external image data may be obtained by a variety of external imaging devices or systems, including angiography devices, computed tomography (CT) devices, x-ray imaging devices, ultrasound imaging devices, or any other suitable imaging device or system.

At step 804, the processor circuit generates a roadmap of the vessel using first external image data. In some embodiments, generating the roadmap includes selecting an image or image frame from the first external image data. For example, the first external image data may include extravascular angiographic images obtained of a vessel when contrast agent is introduced into the vessel. Accordingly, generating the roadmap may include selecting an image from the angiographic image data in which at least a portion of the vessel is shown by the contrast agent. In some embodiments, the processor circuit selects a roadmap image based on an amount of contrast agent seen, a brightness value of the image, a contrast value, or other values derived using image processing. For example, in some embodiments, selecting a roadmap image includes deriving a vesselness value for a plurality of angiographic images. For example, the processor circuit may be configured to perform a segmentation of the plurality of external image frames to determine which of the image frames includes a sufficient amount of blood vessels. In some embodiments, the roadmap is selected by identifying an external image that shows the maximum number of vessels or vessel branches. The processor circuit may employ one or more image processing techniques to identify the roadmap image, including Hessian filters, Frangi filters, segmentation, QCA, etc. Further, in some embodiments, once a roadmap image is selected, generating the roadmap may further include identifying vessels and/or vessel branches in the image. For example, generating the roadmap may include identifying and/or designating vessel boundaries and/or center lines. The vessel boundaries and/or center lines may be identified using, e.g., Hessian filters, Frangi filters, segmentation, QCA, etc. Additional description and details related to generating roadmaps can be found in U.S. Pat. No. 9,770,172, issued Sep. 26, 2017, and U.S. Pat. No. 9,095,308, issued Aug. 4, 2015, the entireties of which are incorporated by reference.

In step 806, the processor circuit identifies or designates a region of interest (ROI) of the vessel on the roadmap. In some embodiments, the ROI may be a vessel branch, or a length of a vessel that is associated with a stenosis, lesion, or collapsing of the vessel walls. In some embodiments, the ROI may be manually selected by a user via a user interface device. For example, the user may select the ROI using a mouse, trackball, track pad, keyboard, touch screen display, or other user interface device while looking at the roadmap image. In some embodiments, identifying the ROI comprises receiving one or more user inputs associated with a proximal and/or distal point of the ROI. For example, in some embodiments, a user may designate or identify the ROI by selecting a first point and a second point on a vessel in the roadmap image such that the ROI is the length of the vessel between the first point and the second point. In some embodiments, the user input may comprise a selection of a single point on a vessel in the roadmap image such that the ROI is identified as a length of the vessel that includes the selected point. In some embodiments, the user input indicates a region of the image, and the processor circuit designates a length of the vessel near the indicated region as the ROI. In some embodiments, the user input indicates a length of the vessel to be designated as the ROI. For example, the user may use a mouse, trackball, trackpad, or any other suitable user interface device to trace a length of the vessel.

Figure 8:
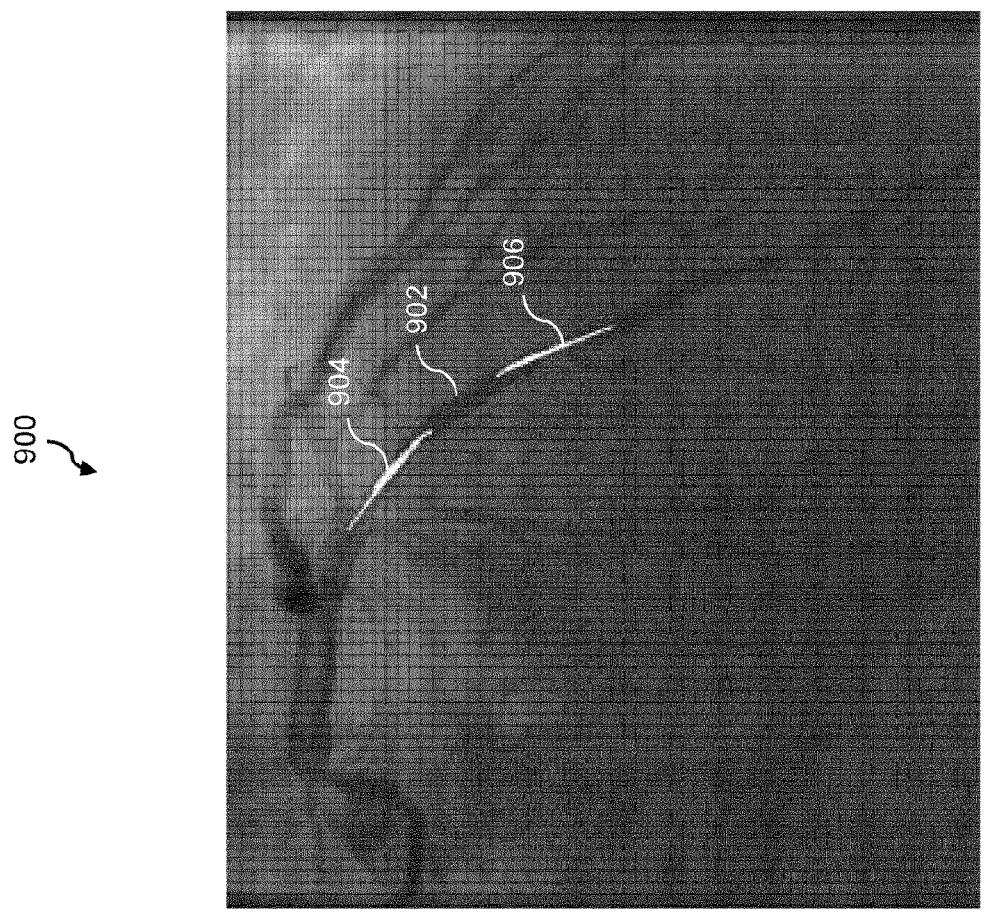
FIG. 8 is a diagrammatic view of an angiographic image with user identified multiple region of interest, according to embodiments of the present disclosure.
Figure 9:
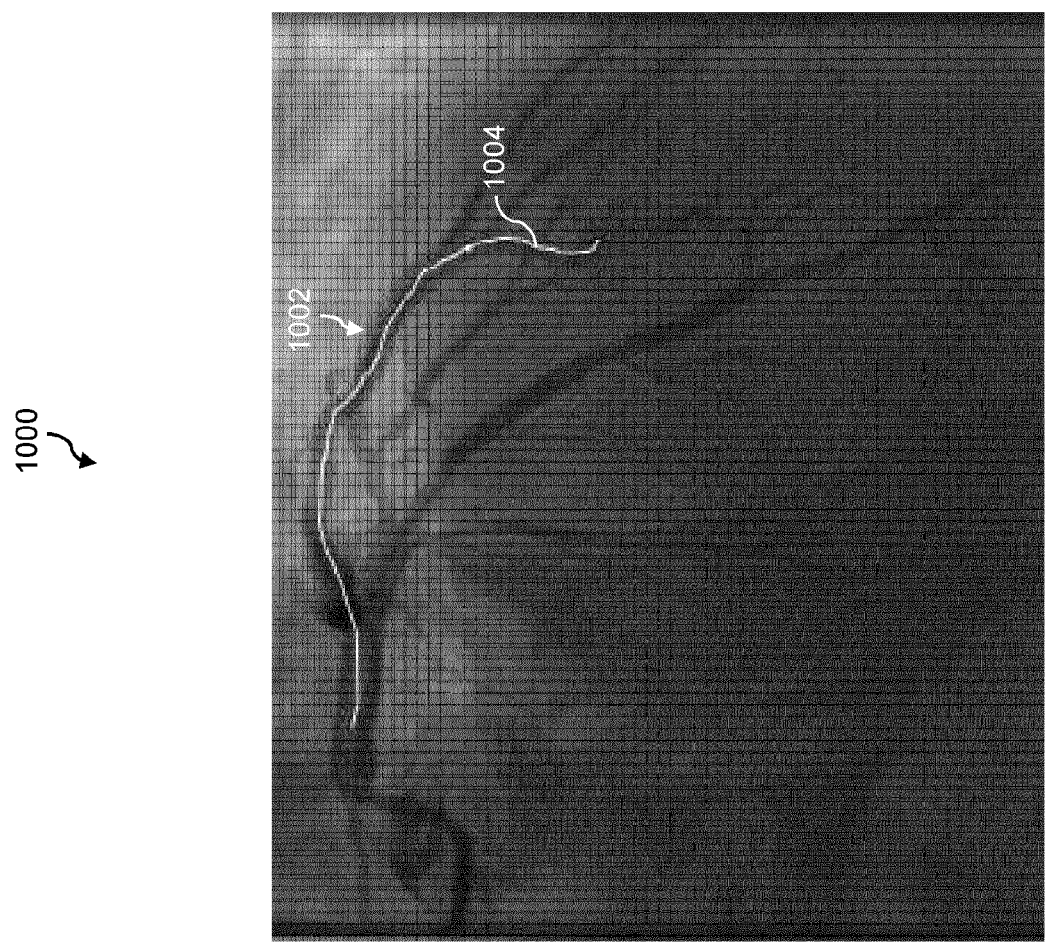
FIG. 9 is a diagrammatic view of an angiographic image with user identified one region of interest, according to embodiments of the present disclosure.

In other embodiments, the processor circuit is configured to identify or designate the ROI automatically by image processing the roadmap image. For example, the processor circuit may be configured to perform a vessel segmentation of the roadmap to identify a narrowed region or portion of the vessel. For example, in some embodiments, the processor circuit may identify one or more ROIs based on identifying a narrowing of a vessel. For example, the processor circuit may determine whether a ratio of the change in diameter over a length of the vessel exceeds a threshold. Further, in some embodiments, the processor circuit is configured to identify more than one ROI. The multiple ROIs may be identified individually based on a user input, or automatically by the processor circuit. In some embodiments, the processor circuit is configured to output a graphical representation of the one or more ROIs to a display device in communication with the processor circuit. In that regard, FIG. 8 shows a roadmap image 900 of a vessel 902 with graphical indicators 904, 906 associated with different ROIs overlaid on corresponding regions of the vessel 902. In some embodiments, the processor circuit generates and outputs the graphical indicators 904, 906 such that they are positioned over a center line of the vessel. In some embodiments, the processor circuit generates and outputs the indicators 904, 906 such that they fill a luminal area of a corresponding region of the vessel. FIG. 9 shows a roadmap image 1000 of a vessel branch 1002 with a graphical indicator 1004 associated with an ROI overlaid on the vessel branch 1004. In this instance, the ROI comprises a continuous and relatively longer segment of the vessel 1002. In the embodiments shown in FIGS. 8 and 9, the indicators 904, 906, and 1004 comprise solid lines. However, it will be understood that other types of indicators could also be used. For example, the indicators 904, 906, 1004 may include dashed lines, dotted lines, shapes, patterns, numerals, text, color, highlights, and/or combinations thereof.

In step 808, the processor circuit receives second external image data representative of an intravascular data acquisition device within the vessel. For example, the second external image data may comprise fluoroscopic image data of the vessel and the intravascular data acquisition device positioned within the vessel. In some embodiments, the second external image data and the first external image data are obtained by the same external imaging device, such as an x-ray imaging device or an ultrasound imaging device. For example, in some embodiments, the first external image data comprises angiographic image data of a vessel obtained by an x-ray imaging device while contrast agent is present in the vasculature. Accordingly, the second external image data may comprise fluoroscopic images obtained by the same x-ray imaging device after the contrast agent has been removed from the imaged vasculature. In other embodiments, the first external image data and the second external image data are obtained by different imaging devices.

In step 810, the processor circuit determines, based on the second external image data, whether the intravascular data acquisition device has entered the ROI. In some embodiments, step 810 further includes co-registering, transforming, or otherwise modifying the second external image data to spatially match the roadmap. In some embodiments, multiple roadmap images are identified or designated and correspond to different times during a physiological cycle of the patient, such as a heart beat or breathing. Accordingly, the second external image data may be gated such that each image or image frame of the second external image data is matched with a roadmap image that was obtained at the same point of the physiological cycle. Step 810 may involve performing one or more image transformations to the second external image data, including distortion, stretching, compression, rotating, magnifying, and/or any other suitable image transformation such that the vasculature structures in the second external image data overlap the vasculature structures in the roadmap.

The processor circuit tracks the location of the intravascular data-acquisition device in the second external image data to determine whether the intravascular data acquisition device has entered the ROI. In that regard, the processor may be configured to co-register the tracked location of the intravascular data acquisition device in the second external image data with the roadmap. Further details and examples for co-registration of extravascular images and/or intravascular data can be found in U.S. Pat. No. 7,930,014, issued Apr. 19, 2011, U.S. Pat. No. 8,298,147, issued Oct. 30, 2012, and U.S. Patent Application Publication No. 2014/0276085, filed Mar. 12, 2014, the entireties of which are incorporated by reference.

Tracking the location of the intravascular data acquisition device may comprise identifying one or more markers of the device in the second external image data. For example, in some embodiments, an intravascular data acquisition device comprises one or more radiopaque markers that appear in fluoroscopic images of the second external image data. By performing image processing on the second external image data, the processor circuit identifies the markers to determine a location of the data acquisition device. Based on identifying the markers, the processor circuit determines the location of the intravascular data acquisition device in the vessel with respect to the roadmap. In some embodiments, the processor circuit determines the location of the device such that the location of the device is mapped to a vessel pathway in the roadmap image. The processor circuit then determines whether the device has entered the region of interest based on the determined location of the intravascular data acquisition device. In some embodiments, determining whether the device has entered the ROI comprises comparing the determined location of the device, with respect to the roadmap, with the location of the ROI. For example, the processor circuit may use a coordinate system (e.g., cartesian coordinate system) in which coordinate values correspond to locations on the roadmap. The processor circuit may compare the coordinate values of the determined location of the device with the range of coordinate values associated with the ROI. If the determined location of the device corresponds to a location of the ROI, the processor circuit may determine that the device has entered the ROI.

In some embodiments, step 812 includes automatically instructing or controlling the intravascular data acquisition device to start obtaining the intravascular data. The intravascular data acquisition device may obtain the intravascular data during a pullback procedure in which the intravascular data acquisition device is pulled back through a segment of the vessel. In some embodiments, step 812 includes initiating a receipt of intravascular data while the intravascular data acquisition device is already obtaining the intravascular data. In some embodiments, step 812 includes generating a time stamp to be assigned to the intravascular data to indicate which intravascular data is representative of the ROI, and which intravascular data is not representative of the ROI. The intravascular data obtained by the intravascular data acquisition device may be co-registered to the roadmap by the processor circuit. Accordingly, each portion or point of the intravascular data is associated with a respective location of the vessel with respect to the roadmap.

As described above, in some embodiments, the processor circuit is further configured to determine whether the intravascular data acquisition device has exited the ROI. In some aspects, the processor circuit may determine whether the device has exited the ROI in a similar manner used to determine whether the device entered the ROI. Accordingly, the processor circuit may continue tracking the location of the intravascular data acquisition device and comparing the tracked location of the device with the ROI. Once the location of the device is determined to be outside the range of locations associated with the ROI, the processor circuit determines that the device has exited the ROI. Accordingly, the processor circuit may cease receiving the intravascular data from the device. In some embodiments, ceasing to receive the intravascular data comprises halting power to a sensor of the device, or sending a command signal to the device to stop obtaining data. In some embodiments, ceasing to receive the intravascular data comprises sending a command signal to stop storage of the intravascular data to memory. In some embodiments, ceasing to receive the intravascular data comprises generating a time stamp when the device exits the ROI.

In step 814, the processor circuit generates and outputs a graphical representation of the intravascular data of the ROI of the vessel to a display in communication with the processor circuit. In some embodiments, the intravascular data comprises one or more of pressure data, flow data, intravascular image data, temperature data, or any other suitable type of data. In that regard, the graphical representation may comprise text, numbers, graphs, or any other suitable representation of the intravascular data. For example, in some embodiments, the intravascular data comprises pressure data, and the processor circuit is configured to compute a pressure ratio or functional metric associated with the ROI. In some embodiments, the processor circuit is configured to compute a plurality of pressure ratios or functional metrics at a plurality of locations across the ROI. In some embodiments, the functional metric comprises FFR, iFR, or any other suitable functional metric or pressure ratio. In other embodiments, the intravascular data comprises IVUS data or OCT data. The processor may be configured to output one or more cross-sectional images of the vessel to the display. Further, the cross-sectional images may be co-registered to the roadmap by the processor circuit such that a user can cause the processor circuit to update the displayed intravascular image by selecting a particular location or point within the ROI on the roadmap.

The present application advantageously addresses simplifying the workflow by automating a of portion of the data acquisition and ability to control the acquisition of intraluminal data by an intraluminal data acquisition device based on a tracked location of the intraluminal data acquisition device. The automation is also possible across a variety of systems used for vessel evaluation assuming a command and communication protocol exists between the systems. Even, further workflow automation can be achieved given an accurate automated vessel segmentation approach based on the angiogram data. Such algorithms could be used to identify the segments of interest in a vessel (as opposed to the user having to identify the segments of interest). The intravascular data acquisition automation would then be based on those segments of interest.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A system for controlling intravascular data acquisition, comprising:
 a processor circuit configured to:
  generate, using first extravascular image data of a vessel, a roadmap of the vessel;
  identify a region of interest of the vessel on the roadmap of the vessel;
  receive second extravascular image data representative of an intravascular data acquisition device positioned within the vessel;
  determine, based on the second extravascular image data, whether the intravascular data acquisition device has entered the region of interest; and
  in response to determining that the intravascular data acquisition device has entered the region of interest, control the intravascular data acquisition device to obtain intravascular data of the region of interest; and
  output, to a display device in communication with the processor circuit, a first graphical representation of the intravascular data of the region of interest.

2. The system of claim 1, wherein the processor circuit is configured to:
 identify, using the second extravascular image data, a radiopaque marker of the intravascular data acquisition device;
 determine, based on identifying the radiopaque marker, a location of the intravascular data acquisition device with respect to the roadmap of the vessel; and
 determine whether the intravascular data acquisition device has entered the region of interest based on the determined location.

3. The system of claim 1, wherein the processor circuit is configured to output, to the display device, a screen display that includes:
 the roadmap;
 the first graphical representation of the intravascular data of the region of interest;
 a second graphical representation of the region of interest on the roadmap; and
 a third graphical representation of a location of the intravascular data acquisition device.

4. The system of claim 1, wherein the processor circuit is further configured to:
 receive, from a user interface device, a user input indicating an area on the roadmap; and
 identify the region of interest of the vessel based on the user input.

5. The system of claim 4, wherein the user input indicates a length of the vessel on the roadmap.

6. The system of claim 1, wherein the first extravascular image data comprises angiographic data, and wherein the processor circuit is further configured to:
 identify the region of interest based on image processing of the angiographic data.

7. The system of claim 1, wherein the intravascular data comprises at least one of pressure data or flow data, and wherein the processor circuit is further configured to:
 compute a functional metric of the vessel at the region of interest based on the at least one of the pressure data or the flow data.

8. The system of claim 7, wherein the functional metric comprises at least one of fractional flow reserve (FFR) or instantaneous wave-free ratio (iFR).

9. The system of claim 1, wherein the intravascular data comprises intravascular image data.

10. The system of claim 1, wherein the processor circuit is further configured to:
 determine, based on the second extravascular image data, whether the intravascular data acquisition device has exited the region of interest; and
 in response to determining that the intravascular data acquisition device has exited the region of interest, stop receiving the intravascular data of the region of interest of the vessel from the intravascular data acquisition device.

11. The system of claim 1, further comprising the intravascular data acquisition device, wherein the intravascular data acquisition device comprises a flexible elongate member having a proximal portion and a distal portion, and a sensing component coupled to the distal portion, wherein the distal portion and sensing component are configured to be positioned within the vessel.

12. The system of claim 1, wherein the processor circuit is further configured to:
 identify a further region of interest of the vessel on the roadmap of the vessel;
 determine, based on the second extravascular image data, whether the intravascular data acquisition device has entered the further region of interest; and
 in response to determining that the intravascular data acquisition device has entered the further region of interest, control the intravascular data acquisition device to obtain intravascular data of the further region of interest; and
 output, to a display device in communication with the processor circuit, a fourth graphical representation of the intravascular data of the further region of interest.

13. A method, comprising:
 generating, using a first extravascular image data of a vessel, a roadmap of the vessel;
 identifying a region of interest of the vessel on the roadmap of the vessel;
 receiving second extravascular image data representative of an intravascular data acquisition device positioned within the vessel;
 determining, based on the second extravascular image data, whether the intravascular data acquisition device has entered the region of interest; and
 in response to determining that the intravascular data acquisition device has entered the region of interest, receiving intravascular data of the region of interest of the vessel from the intravascular data acquisition device.

14. The method of claim 13, further comprising:
identifying, using the second extravascular image data, a radiopaque marker of the intravascular data acquisition device;
determining a location of the intravascular data acquisition device with respect to the roadmap of the vessel; and
determining whether the intravascular data acquisition device has entered the region of interest based on the determined location.

15. The method of claim 13, further comprising outputting, to a display device, a screen display that includes:
the roadmap;
a graphical representation of the region of interest on the roadmap; and
a second graphical representation of a location of the intravascular data acquisition device.

16. The method of claim 13, further comprising:
receiving, from a user interface device, a user input indicating an area on the roadmap; and
identifying the region of interest of the vessel based on the user input.

17. The method of claim 13, wherein the first extravascular image data comprises angiographic data, and wherein identifying the region of interest comprises identifying the region of interest based on image processing of the angiographic data.

18. The method of claim 13, wherein the intravascular data comprises at least one of pressure data or flow data, and wherein the method further comprises:
computing a functional metric of the vessel at the region of interest based on the at least one of the pressure data or the flow data.

19. The method of claim 18, wherein the functional metric comprises at least one of fractional flow reserve (FFR) or instantaneous wave-free ratio (iFR).

20. The method of claim 13, further comprising:
determining, based on the second extravascular image data, whether the intravascular data acquisition device has exited the region of interest; and
in response to determining that the intravascular data acquisition device has exited the region of interest, stopping receipt of the intravascular data of the region of interest of the vessel from the intravascular data acquisition device.

* * * * *